US010047054B2

(12) United States Patent
Kaplan

(10) Patent No.: US 10,047,054 B2
(45) Date of Patent: Aug. 14, 2018

(54) METHOD FOR THE PRODUCTION OF MDI DIMER

(71) Applicant: EMS-PATENT AG, Domat/Ems (CH)

(72) Inventor: Andreas Kaplan, Chur (CH)

(73) Assignee: EMS-PATENT AG, Domat/Ems (CH)

( * ) Notice: Subject to any disclaimer, the term of this patent is extended or adjusted under 35 U.S.C. 154(b) by 140 days.

(21) Appl. No.: 14/078,134

(22) Filed: Nov. 12, 2013

(65) Prior Publication Data
US 2014/0135458 A1 May 15, 2014

(30) Foreign Application Priority Data

Nov. 13, 2012 (EP) .................................... 12192416

(51) Int. Cl.
C07D 229/00 (2006.01)
C08G 18/82 (2006.01)

(52) U.S. Cl.
CPC ........... C07D 229/00 (2013.01); C08G 18/82 (2013.01)

(58) Field of Classification Search
CPC .............................. C07D 229/00; C08G 18/82
See application file for complete search history.

(56) References Cited

U.S. PATENT DOCUMENTS

| 2,671,082 | A | * | 3/1954 | Stallmann | 540/202 |
|---|---|---|---|---|---|
| 3,489,744 | A | | 1/1970 | Schwarcz et al. | |
| 4,381,332 | A | | 4/1983 | Fulmer et al. | |
| 4,477,619 | A | | 10/1984 | Lattimer et al. | |
| 4,521,338 | A | * | 6/1985 | Grogler et al. | 540/202 |
| 4,569,963 | A | | 2/1986 | Hiroshi et al. | |
| 4,720,545 | A | * | 1/1988 | Grogler et al. | 540/202 |
| 4,740,528 | A | | 4/1988 | Garvey et al. | |
| 4,742,095 | A | | 5/1988 | Markusch et al. | |
| 5,149,766 | A | * | 9/1992 | Bruchmann | 528/49 |
| 5,484,916 | A | | 1/1996 | Bruchmann et al. | |
| 5,565,527 | A | | 10/1996 | Bruchmann et al. | |
| 5,959,027 | A | | 9/1999 | Jakubowski et al. | |
| 6,084,018 | A | | 7/2000 | Wildburg et al. | |
| 6,482,889 | B1 | | 11/2002 | Kurz | |
| 6,506,832 | B1 | | 1/2003 | Derian et al. | |
| 7,705,088 | B2 | | 4/2010 | Durairaj et al. | |
| 8,134,014 | B2 | | 3/2012 | Richter et al. | |
| 8,993,662 | B2 | | 3/2015 | Kaplan | |
| 2002/0193508 | A1 | | 12/2002 | Derian et al. | |
| 2004/0249062 | A1 | | 12/2004 | Derian et al. | |
| 2007/0205393 | A1 | | 9/2007 | Durairaj et al. | |
| 2007/0243375 | A1 | | 10/2007 | Kohashi et al. | |
| 2009/0143558 | A1 | * | 6/2009 | Richter | C07D 229/00 528/54 |
| 2012/0115993 | A1 | | 5/2012 | Kaplan | |
| 2015/0051343 | A1 | | 2/2015 | Kaplan | |

FOREIGN PATENT DOCUMENTS

| CN | 1981083 A | 6/2007 |
|---|---|---|
| CN | 101250251 A | 8/2008 |
| CN | 101296974 A | 10/2008 |
| CN | 101395195 A | 3/2009 |
| CN | 101450928 A | 6/2009 |
| DE | 199 13 042 A1 | 10/2000 |
| DE | 102004038784 A1 | 2/2006 |
| EP | 0 137 427 A2 | 4/1985 |
| EP | 0 739 961 A1 | 10/1996 |
| EP | 0 835 891 A1 | 4/1998 |
| EP | 1 038 899 A1 | 9/2000 |
| EP | 2 159 241 A1 | 3/2010 |
| EP | 2 450 389 A1 | 5/2012 |
| JP | S42-002896 Y1 | 2/1967 |
| JP | S58-039666 A | 3/1983 |
| JP | S59093774 A | 5/1984 |
| JP | H02-151619 A | 6/1990 |
| JP | H03-118367 A | 5/1991 |
| JP | H06-056755 A | 3/1994 |
| JP | H09-12556 A | 1/1997 |
| JP | 09-328474 A | 12/1997 |
| JP | 2000-303054 A | 10/2000 |
| JP | 2005-531677 A | 10/2005 |
| JP | 2009-528347 A | 8/2009 |
| NZ | 228773 A | 7/1991 |
| WO | WO 94/22935 A1 | 10/1994 |
| WO | WO 02/50148 A2 | 6/2002 |
| WO | WO 2007/100399 A1 | 9/2007 |

(Continued)

OTHER PUBLICATIONS

European Patent Office, Notice Pursuant to Article 94(3) IPC in European Patent Application No. 12 192 416.1 (dated May 7, 2015).
European Patent Office, Notice Pursuant to Article 94(3) EPC in European Patent Application No. 12 192 416.1 (dated Nov. 19, 2014).
State Intellectual Property Office of the People'S Republic of China, First Office Action in Chinese Patent Application No. 201310561355.3 (dated Jun. 7, 2016).
Sate Intellectual Property Office of People'S Republic of China, Second Office Action issued in Chinese Application No. 201310561355.3 (dated Mar. 16, 2017).
Japanese Patent Office, Notification of Reasons for Refusal issued in Japanese Application No. 2013-234184 (dated Feb. 22, 2017).

(Continued)

Primary Examiner — Rabon Sergent

(74) Attorney, Agent, or Firm — Leydig, Voit & Mayer, Ltd.

(57) ABSTRACT

The invention relates to a method for the production of 4,4'-methylenebis(phenylisocyanate) dimer (MDI dimer) which is distinguished by an MDI dimer being obtained which is present in high purity. The MDI dimer which is produced according to the method according to the invention is distinguished by being essentially free of MDI and also urea derivatives. Furthermore, the invention relates to a corresponding MDI dimer and also the use thereof as crosslinker for polyurethanes.

21 Claims, 1 Drawing Sheet

(56) References Cited

FOREIGN PATENT DOCUMENTS

WO    WO 2010/085602 A1    7/2010

OTHER PUBLICATIONS

Federal Institute of Industrial Property, Office Action in Russian Patent Application No. 2013148660/04 (dated Aug. 23, 2017).
State Intellectual Property Office of People'S Republic of China, Third Office Action issued in Chinese Application No. 201310561355.3 (dated Sep. 5, 2017).
Federal Institute of Industrial Property, Office Action in Russian Patent Application No. 2013148660/04 (dated Dec. 15, 2017).

* cited by examiner

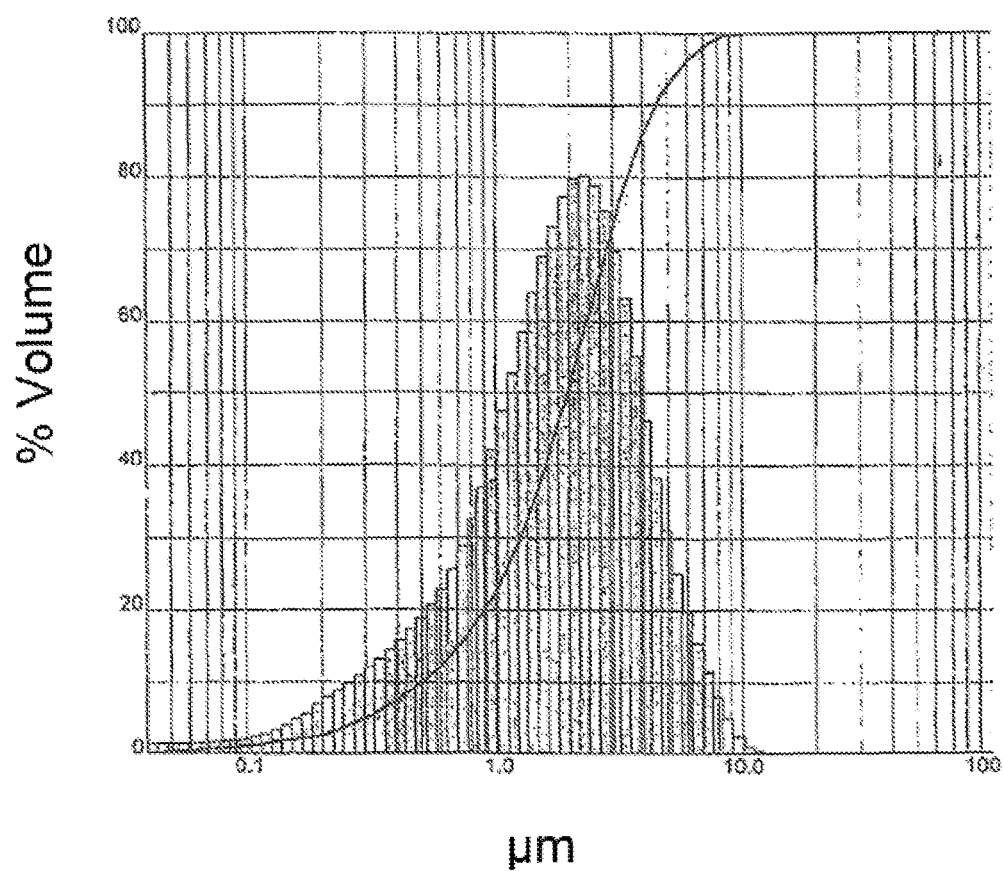

METHOD FOR THE PRODUCTION OF MDI DIMER

CROSS-REFERENCE TO A RELATED APPLICATION

This patent application claims the benefit of European Patent Application No. EP 12 192 416.1, filed Nov. 13, 2012, the disclosure of which is incorporated herein by reference.

FIELD OF THE INVENTION

The invention relates to a method for the production of 4,4'-methylenebis(phenylisocyanate) dimer (MDI dimer) which is distinguished by an MDI dimer being obtained which is present in high purity. The MDI dimer which is produced according to the method according to the invention is distinguished by being essentially free of MDI and also urea derivatives. Furthermore, the invention relates to a corresponding MDI dimer and also the use thereof as crosslinker for polyurethanes.

4,4'-methylenebis(phenylisocyanate) dimers (MDI dimer) are known. The 4,4'-MDI dimer has the CAS No. 17589-24-1.

A method for the production of an MDI dimer is already known from JP 09-328 474 of Nippon Polyurethanes. In the case of this method, the MDI is dissolved firstly in ethylacetate and mixed with a catalyst. The MDI dimer is then filtered off after 24 hours. As emerges from JP 09-328 474 (see example 3), the reaction product consists however only of up to 81% of the MDI dimer. The MDI dimer obtained according to the Japanese document hence has also high proportions of MDI monomer or urea derivatives. Such MDI dimers are therefore suitable also as crosslinkers for polymers only in a restricted manner.

For many applications, in particular for use as crosslinker for polymers, it is however important that the 4,4'-MDI dimer is present in high purity. In particular for use as crosslinker for polyurethanes, the requirement exists of making available a 4,4-MDI dimer which is free of MDI monomer and urea derivatives. For such applications, it is also important that the MDI dimer can be readily stored and is available in a uniform grain size.

SUMMARY OF THE INVENTION

Starting herefrom, it is the object of the present invention to make available a method for the production of a 4,4'-MDI dimer which leads to a product with high purity. It is thereby desired that the 4,4'-MDI dimer is free of MDI monomer and of urea derivatives. Furthermore, the invention comprises a corresponding 4,4'-MDI dimer and also the use of the 4,4'-MDI dimer as crosslinker for polyurethanes.

This object is achieved by the features of the MDI dimer and by the method for production described herein, and the advantageous developments thereof. Uses according to the invention are also described.

BRIEF DESCRIPTION OF THE DRAWING

FIGURE. 1 depicts the particle size distribution of an MDI dimer produced according to the invention.

DETAILED DESCRIPTION OF THE INVENTION

The method according to the invention is distinguished by providing, in a first method step a), a solvent which already comprises a catalyst, the solvent being selected such that it is suitable as solvent for 4,4-methylenebis(phenylisocyanate). In the case of this first method step, it is necessary in addition that the operation takes place in an inert gas atmosphere at as low temperatures as possible, namely at >25° C. to max. 45° C.

In the next method step b), melted and/or dissolved 4,4-methylenebis(phenylisocyanate), i.e. MDI, is added with stirring. The product then begins subsequently to precipitate.

Subsequently, the reaction is then interrupted by addition of a deactivator (method step c)). In the case of this method step, it is crucial that, after stopping the reaction, stirring continues to take place for a certain timespan. This timespan is in the range of 0.5 to 1.5 hours.

Subsequent to this method step, the MDI dimer is separated from the solvent (method step d)) and purified in method step e).

In the case of the method according to the invention, it is thereby particularly important that the precise sequence of the above-described method steps a) to e) is maintained exactly. Of particular importance thereby is the reaction management, in particular with respect to the temperature level. It is essential that, as indicated in method step a), a temperature which is in the range >25° C. to 45° C. is maintained.

It is thereby preferred if the temperature in method step a) is maintained at 30 to 40° C.

For the addition of the melted and/or dissolved MDI, addition in drops is preferred.

Provision of the solvent comprising the catalyst is effected under an inert gas atmosphere, the inert gas being selected from nitrogen, argon and/or helium. Preferably, the water content of these inert gases is thereby adjusted to max. 0.01% by volume, preferably to max. 0.005% by volume.

Suitable catalysts which are contained in the solution according to method step a) are selected from tertiary phosphines, amino-substituted phosphines, imidazoles, guanidines, pyridines substituted in position 3 or 4, pyridines substituted in position 3 and 4, cyclic amidines, antimony pentafluoride, boron trifluoride or mixtures thereof.

Preferably there are used as catalysts, tertiary, aliphatic or mixed aliphatic-aromatic phosphines, trialkylphosphines, tris(N,N-dialkylamino)phosphines, dialkylimidazoles, 4-N,N-dialkylaminopyridines, pyridines which are substituted by N atoms in position 3 and 4 and which are connected via carbon segments—preferably binary, saturated carbon segments or mixtures thereof.

There are used for particular preference as catalysts, tris(N,N-dialkylamino)phosphines, 1,2-dialkylimidazoles, 4-N,N-dialkylaminopyridines or mixtures thereof.

There are used for very particular preference as catalysts, tris(N,N-dimethylamino)phosphine, tris(N,N-diethylamino)phosphine, 4-N,N-dimethylaminopyridine, 4-N,N-diethylaminopyridine, 1,2-dimethylimidazole, 1,2-diethylimidazole or mixtures thereof.

Phosphines are also termed phosphanes or phosphoranes.

As deactivator for stopping the reaction (method step c)), all deactivators which are common per se can be used. Examples of these are strong acids, acid chlorides, acid anhydrides or alkylation agents.

There are used preferably as deactivator, chloroacetic acid, trichloroacetic acid, trifluoroacetic acid, methanesulphonic acid, perfluorobutanesulphonic acid, phosphoric acid, chloroformic acid, benzoyl chloride, dimethylcarbamide acid chloride, acetic acid anhydride, succinic acid anhydride, dimethylsulphate, methyliodide, toluenesulphonic acid methyl ester or mixtures thereof.

Benzoyl chloride is used for particular preference as deactivator.

The separation of the MDI dimer from the solvent (method step d)) is effected with one or with a combination of a plurality of mechanical separation methods for solid-liquid separation. Preferably the at least one mechanical separation method is selected from the group consisting of sedimentation, filtration, centrifugation and separation with cyclones.

In the case of sedimentation, the separation can be effected by means of gravitation or centrifugal force.

In the case of filtration, the separation can be effected by gravitation, centrifugal force or pressure differences. Pressure differences can concern low pressure (vacuum) or high pressure.

The filtration can be effected by means of vacuum filtration, rotary disc filters, drum filters, leaf filters, plate filters, band filters, screw clearance filters, filter presses, membrane filter presses, band presses or combinations thereof.

The centrifugation can be effected by means of solid wall screw conveyor centrifuges, disc centrifuges, rotary disc centrifuges, trailing-blade centrifuges, push-type centrifuges, bowl centrifuges, decanter centrifuges, separators or combinations thereof.

Hydrocyclones are used preferably in the case of separation with cyclones.

Subsequent to method step e), as is also known already from the state of the art, drying of the MDI dimer can be effected, which is implemented preferably at 40° C. to 60° C. in a vacuum or inert gas flow for 12 to 24 hours. For particular preference, the drying is effected at 40° C. to 50° C. in a vacuum for 12 to 20 hours.

Preferably, the MDI dimer is dried after method step e).

Solvents which are suitable for the method according to the invention are solvents which are able to dissolve the MDI monomer completely at the indicated reaction temperatures, i.e. at >25° C. to 45° C. The water content of the solvent must be at most 0.04% by weight, preferably at most 0.02% by weight, particularly preferred at most 0.01% by weight.

Examples of solvents are acetone, N-methylpyrrolidone, benzene, ethylacetate, acetonitrile, nitromethane, kerosine, octane or mixtures hereof.

The inventors were thereby able to show that ethylacetate is particularly suitable as solvent. In the case of the method according to the invention, preferably the operation takes place, during purification of the MDI dimer, with the same solvent as that also used for the reaction. Preferably, ethylacetate is thereby used hence both for the MDI monomer and for the purification step.

Furthermore, the invention relates to a 4,4'-methylenebis (phenylisocyanate) dimer which can be produced according to a method as described above. The MDI dimer according to the invention is distinguished by being essentially free of monomeric MDI. There is understood by essentially free of monomeric MDI that the MDI dimer comprises less than 1% by weight, preferably less than 0.5% by weight, particularly preferred less than 0.1% by weight, very particularly preferred less than 0.08% by weight, of monomeric MDI. The MDI dimer according to the invention has in addition no proportions of products which can be detected with HPLC-MS (High Performance Liquid Chromatography Mass Spectrometry Combination) with UV detector and mass detector, such as trimers, tetramers, pentamers or even higher oligomers. The MDI dimer according to the invention is also essentially free of urea derivatives. There is understood by essentially free of urea derivatives that the MDI dimer comprises less than 10% by weight, preferably less than 7% by weight, particularly preferred less than 4% by weight, very particularly preferred less than 2% by weight, of urea derivatives.

The highly pure MDI dimer according to the invention is made available, according to the invention, preferably in a powder form. In addition, the MDI dimer can be subjected, after method step d) (separation of the obtained MDI dimer from the solvent) and the purification of the obtained MDI dimer with the solvent (method step e)), also to a grinding process so that then an average granulate size $d_{50}$ of the powders is present, which is in the range between 1 and 4 μm, preferably at 2 μm.

The highly pure MDI dimer according to the invention is particularly suitable as crosslinker for polymers and, here in particular, for polyurethanes for the production of foam- and insulating materials, e.g. as soft-, hard- or integral foam, or of unfoamed solid or rubber-elastic materials for commercial articles, such as e.g. seating, casting resins, paint resins, sealing materials, adhesive resins or coating materials for synthetic leather and textile aids. It has been shown that the MDI dimer according to the invention has an extremely high reaction capacity and then leads to end products which have excellent mechanical properties after the crosslinking.

The invention is explained in more detail subsequently with reference to a general embodiment and a special production example and also with reference to FIG. 1.

FIG. 1 shows the particle size distribution of an MDI dimer produced according to the invention, which has been subjected to another grinding after method step e). As emerges from FIG. 1, the MDI dimer in this case has a very narrow size distribution. An MDI dimer in a highly pure form, as described above, in combination with the very fine particle distribution is suitable particularly well as crosslinker for polyurethanes. A very high reactivity was thereby established, which is attributed, on the one hand, to the high purity and, on the other hand, to the particle size distribution. Furthermore, an MDI dimer, as described above, has excellent storage properties and therefore is particularly well suited as crosslinker for polyurethanes.

The production of the MDI dimer is effected in solution in an inert atmosphere with water exclusion at 30 to 40° C. The solvent comprising the dissolved catalyst is placed therein. In addition, MDI which is melted or dissolved is added in drops with stirring within 0.5 to 3 h. After approx. half of the addition, the product begins to precipitate. After the adding in drops, stirring takes place at the reaction temperature for another 1 to 4 h. Subsequently, the reaction is interrupted by addition of the deactivator, stirring taking place at the reaction temperature for a further 0.5 to 1.5 h after the addition. The batch is filtered through a glass- or ceramic frit in a vacuum after cooling to room temperature and subsequently is washed at least twice with solvent. Drying takes place in a vacuum or inert gas flow at 40 to 60° C. for 12 to 24 h.

The thus produced MDI dimer comprises neither trimers, tetramers, pentamers nor higher oligomers which can be detected by means of HPLC-MS with UV detector and mass detector.

There are used as inert gases, nitrogen, argon or helium, the water content of which is at most 0.01% by vol.

The solvent is dried to a water content of at most 0.04% by weight.

Should melted MDI be used for the reaction, it is melted at at most 60° C., preferably at 45 to 55° C.

Determination of the content of monomeric MDI in the MDI dimer:

The monomeric MDI is extracted from the MDI dimer and derivatised with ethanol in the extract.

The MDI dimer is extracted for this purpose with 25 ml ethylacetate in a 50 ml round-bottomed flask for five hours at 23° C., stirring taking place with a magnetic stirrer. The extract is filtered and the filtrate is transferred into a 50 ml measuring flask. Subsequently, the extract is filled with ethanol to 50 ml, left to stand for 30 min. at 23° C., filtered and decanted into a glass flask.

This process is implemented with a low initial weight (1 mg MDI dimer per ml ethylacetate) and with a high initial weight (25 mg MDI dimer per ml ethylacetate).

Determination of the concentration of monomeric MDI in the extract is effected with HPLC (High Performance Liquid Chromatography) according to the method of the external standard.

As HPLC apparatus, an Acquity UPLC of the company Waters Corp. is thereby used, as column, BEH C18 by Waters Corp. (10.0 cm long, internal diameter 2.1 mm, particle size of the filling 1.7 μm. An acetonitrile/water gradient mixture with a flow rate of 0.4 ml/min serves as elution agent. Detection is effected with a UV detector at a wavelength of 254 nm.

MDI is used as external standard. At least 3 initial weights are weighed in, dissolved in 50 ml ethylacetate/ethanol 1/1 (vol/vol) and decanted. The calibration straight line is produced with the software Empower 2 of Waters Corp. and must have a correlation coefficient of at least 0.999.

The content of monomeric MDI in % by weight is calculated according to the following formula:

$$\text{Monomeric } MDI = ([(KA-KB) \times V] : EA) \times 100$$

KA concentration of the monomeric MDI in mg/ml with a high initial weight
KB concentration of the monomeric MDI in mg/ml with a low initial weight
V volume ethyl acetate in ml
EA initial weight of the MDI dimer with a high initial weight in mg Acetonitrile, ethanol and ethylacetate are used with purity p.a. (for the analysis). The water is twice-distilled water.

The arithmetic average of three measurements is indicated.

Determination of the purity of the MDI dimer

The purity of the MDI dimer is determined with HPLC-MS (High Performance Liquid Chromatography Mass Spectrometry Combination) with UV detector and mass detector, the correspondence of the peaks being effected via the mass. The purity of the MDI dimer is indicated in % by area (% by area), the total area of all the peaks thereby corresponds to 100% by area. The indicated values are the arithmetic average of three measurements.

10 mg of the MDI dimer is dissolved for this purpose in a mixture of 5 ml tetrahydrofurane and 5 ml methanol at 23° C., left to stand for another 30 min. thereafter for derivatisation with the methanol, filtered and decanted into a glass flask.

There is used as HPLC apparatus, an Acquity UPLC of the company Waters Corp., as column, BEH C18 of the Waters Corp. (10.0 cm long, internal diameter 2.1 mm, particle size of the filling 1.7 μm). An acetonitrile/water gradient mixture serves as elution agent. The UV detector operates at 254 nm and the mass detector SQ in the ESI mode (Electro-Spray-Ionisation mode).

Acetonitrile, methanol and tetrahydrofurane are used with purity p.a. (for the analysis). The water is twice-distilled water.

Production examples for 4,4'-methylenebis(phenylisocyanate) dimer:

The reaction apparatus consists of a double-walled, cylindrical reaction vessel (volume 1 l) with a base discharge valve, stirrer, ground cover, three dropping funnels, two thereof double-walled, one G4 frit connected to the base discharge valve and a vacuum pump.

The apparatus is made inert three times alternately with vacuum (30 mbar) and nitrogen. The entire production of the MDI dimer takes place under a nitrogen stream.

In the reaction vessel temperature-controlled to 35° C., 500 ml ethylacetate in which 1.0 g 4-N,N-dimethylaminopyridine is dissolved is introduced by means of a dropping funnel and temperature-controlled in the reaction vessel to 35° C.

130.0 g MDI melted in the circulating air oven at 50° C. are added via a dropping funnel temperature-controlled to 50° C. within 45 minutes with stirring. It is thereby ensured that the temperature of the reaction mixture remains at 35° C. After approx. half of the addition, the product begins to precipitate.

Subsequent to the MDI addition, stirring takes place for another 2 hours at 35° C.

Thereafter, 1.27 g benzoyl chloride, dissolved in 5 ml ethylacetate, is added via a dropping funnel temperature-controlled to 35° C. within 10 minutes with stirring and is stirred for a further 15 min.

Subsequently, the batch is cooled to 23° C. and filtered at 550 mbar through the G4 frit. The product is washed twice with respectively 100 ml ethylacetate and dried at 50° C. and 30 mbar for 16 h.

Yield 120.5 g, i.e. 92.7% by weight, relative to the MDI initial weight.

The product comprises:

| | | |
|---|---|---|
| 0.07 | % by weight | monomeric MDI* |
| 99.5 | % by area | MDI dimer, derivatised** |
| 0.5 | % by area | urea dimer, derivatised** |

*determined by extraction and subsequent HPLC
**determined by HPLC-MS, indicated in % by area (% by area).

The invention claimed is:

1. A method for the production of 4,4'-methylenebis(phenylisocyanate) dimer (MDI dimer) having the following steps in the following order:
   a) providing only one solvent for 4,4'-methylenebis(phenylisocyanate) (MDI) in an inert gas atmosphere, said only one solvent and said inert gas being maintained at >25° C. to 45° C., and the only one solvent comprising a dimerization catalyst,
   b) adding a melted MDI and/or MDI dissolved in a solvent consisting of the same solvent as the only one solvent of step a) with stirring over a timespan of 0.5 to 3 hours,
   c) adding a deactivator for stopping the dimerization, with the proviso that stirring takes place in addition over a timespan of 0.5 to 1.5 hours at a temperature of >25° C. to 45° C., wherein the deactivator is selected from the group consisting of strong acids, acid chlorides, and acid anhydrides,
   d) separating the obtained MDI dimer from the only one solvent and e) purifying the obtained MDI dimer, wherein during the purification of the MDI dimer, the solvent utilized consists of the same solvent as the only one solvent of step a) and the MDI is washed twice with the same solvent;

wherein the only one solvent of step a) is selected from the group consisting of acetone, N-methylpyrrolidone, benzene, ethylacetate, acetonitrile, nitromethane, kerosine, and octane; and the water content of the only one solvent is maximum 0.04% by weight, and wherein the MDI dimer produced by the method has a monomeric MDI content of less than 0.1 wt.-%.

2. The method according to claim 1, wherein, in step a), a temperature in the range of 30° C. to 40° C. is maintained and the melted and/or the dissolved MDI is added in step b) in drops.

3. The method according to claim 1, wherein the inert gas is selected from nitrogen, argon and helium.

4. The method of claim 3, wherein the nitrogen, argon and/or helium has a water content of max. 0.01% by volume.

5. The method according to claim 1, wherein the dimerization catalyst is selected from the group consisting of tertiary phosphines, amino-substituted phosphines, imidazoles, guanidines, pyridines substituted in position 3 or 4, pyridines substituted in positions 3 and 4, cyclic amidines, antimony pentafluoride, boron trifluoride and mixtures thereof.

6. The method of claim 5, wherein the dimerization catalyst is selected from the group consisting of tertiary, aliphatic or mixed aliphatic-aromatic phosphines, trialkylphosphines, tris(N,N-dialkylamino)phosphines, dialkylimidazoles, 4-N,N-dialkylaminopyridines, pyridines which are substituted by N atoms in positions 3 and 4 and which are connected via carbon segments, and mixtures thereof.

7. The method of claim 6, wherein the dimerization catalyst is selected from the group consisting of tris(N,N-dialkylamino)phosphines, 1,2-dialkylimidazoles, 4-N,N-dialkylaminopyridines and mixtures thereof.

8. The method of claim 7, wherein the dimerization catalyst is selected from the group consisting of tris(N,N-dimethylamino)phosphine, tris(N,N-diethylamino)phosphine, 4-N,N-dimethylaminopyridine, 4-N,N-diethylaminopyridine, 1,2-dimethylimidazole, 1,2-diethylimidazole and mixtures thereof.

9. The method of claim 6, wherein the carbon segments are binary, saturated carbon segments.

10. The method according to claim 1 wherein the separation of the reaction product in step d) is effected by one or a combination of a plurality of mechanical separation methods for solid-liquid separation.

11. The method of claim 1, wherein the deactivator is selected from the group consisting of chloroacetic acid, trichloroacetic acid, trifluoroacetic acid, methane sulphonic acid, perfluorobutane sulphonic acid, phosphoric acid, chloroformic acid, benzoyl chloride, dimethyl carbamide acid chloride, acetic acid anhydride, succinic acid anhydride, and mixtures thereof.

12. The method of claim 11, wherein the deactivator is benzoyl chloride.

13. The method of claim 1, wherein the only one solvent is ethyl acetate.

14. The MDI dimer obtained by a method according to claim 1, wherein the MDI dimer has a content of monomeric MDI of less than 0.08% by weight.

15. The MDI dimer according to claim 14, wherein said MDI dimer comprises no oligomeric products.

16. The MDI dimer of claim 15, wherein the oligomeric products are trimers, tetramers, pentamers, and higher oligomers.

17. The MDI dimer according to claim 15, wherein the MDI dimer is present in powder form.

18. The MDI dimer according to claim 17, wherein the powder is composed of granulates and the average diameter $d_{50}$ of the granulates is in a range between 1 and 4 µm.

19. A method for cross-linking a polymer comprising reacting the MDI dimer of claim 14 with the polymer.

20. A method for the production of 4,4'-methylenebis (phenylisocyanate) dimer (MDI dimer) consisting of the following steps in the following order:

a) providing only one solvent for 4,4'-methylenebis(phenylisocyanate) (MDI) in an inert gas atmosphere, said only one solvent and said inert gas being maintained at >25° C. to 45° C., and the only one solvent comprising a dimerization catalyst; subsequently b) adding a melted MDI and/or MDI dissolved in a solvent consisting of the same solvent as the only one solvent of step a) with stirring over a timespan of 0.5 to 3 hours; subsequently c) adding a deactivator for stopping the dimerization, with the proviso that stirring takes place in addition over a timespan of 0.5 to 1.5 hours at a temperature of >25° C. to 45° C., wherein the deactivator is selected from the group consisting of strong acids, acid chlorides, and acid anhydrides; subsequently d) separating the obtained MDI dimer from the only one solvent; and subsequently e) purifying the obtained MDI dimer by solvent washing, wherein during the purification of the MDI dimer, the solvent utilized consists of the same solvent as the only one solvent of step a);

wherein the only one solvent is selected from the group consisting of acetone, N-methylpyrrolidone, benzene, ethylacetate, acetonitrile, nitromethane, kerosine, and octane; and the water content of the only one solvent is maximum 0.04% by weight, wherein the MDI dimer produced by the method has a monomeric MDI content of less than 0.1 wt.-%.

21. The method of claim 20, wherein the only one solvent is ethyl acetate.

* * * * *